United States Patent [19]

Cohen et al.

[11] 4,432,906

[45] Feb. 21, 1984

[54] INHIBITORS OF SRS-SYNTHESIS

[75] Inventors: Noal Cohen, Montclair; Giuseppe Weber, Cedar Grove, both of N.J.

[73] Assignee: Hoffmann-La Roche Inc., Nutley, N.J.

[21] Appl. No.: 301,613

[22] Filed: Sep. 14, 1981

[51] Int. Cl.[3] .......................... C11C 3/02; A61K 31/23
[52] U.S. Cl. .................. 260/410.9 R; 260/413; 560/205; 568/420; 568/579; 424/312; 424/313
[58] Field of Search ...................... 260/410.9 M, 413 L

[56] References Cited

U.S. PATENT DOCUMENTS

| | | | |
|---|---|---|---|
| 2,934,570 | 7/1960 | Goldberg et al. | 260/410.9 M X |
| 3,450,821 | 6/1969 | Carstensen et al. | 260/413 L X |
| 3,952,035 | 4/1976 | Galantay et al. | 260/413 L |
| 3,972,907 | 8/1976 | Baran et al. | 260/410.9 M |

OTHER PUBLICATIONS

Heslinga et al., CA 85: 93754s, (1976).
Fryer et al., CA 82: 97629r, (1975).
Liang et al., CA 93: 25952v, (1980).
Yeh et al., Tetrahedron Letters, No. 49, pp. 4257–4260, (1977).
Carl D. Perchonock, Tetrahedron Letters, 24, pp. 2457–2460, 1983.

*Primary Examiner*—Thomas A. Waltz
*Attorney, Agent, or Firm*—Jon S. Saxe; George M. Gould; William H. Epstein

[57] ABSTRACT

Methyl derivatives of arachidonic acid and intermediates thereto have been synthesized. These derivatives are inhibitors of SRS-A synthesis and are useful for treating and preventing allergic reactions.

3 Claims, No Drawings

INHIBITORS OF SRS-SYNTHESIS

BACKGROUND OF THE INVENTION

In mammals, essential fatty acids, such as arachidonic acid, serve as substrates for cellular biological processes producing prostaglandins and the material SRS-A (Slow Reacting Substance of Anaphylaxis), the pathway to prostaglandins being catalyzed by prostaglandin synthetase and the pathway to SRS-A being catalyzed by lipoxygenase. The prostaglandin pathway leads to products of known beneficial function in mammals, while the SRS-A pathway produces products which have no known beneficial function in mammals.

After its cellular biosynthesis, SRS-A is released from the cell of origin and produces effects, such as bronchoconstriction, during an allergic response. There has been an ongoing need for agents that will specifically inhibit the synthesis of SRS-A by mammalian cells in order to prevent the release of SRS-A and the resulting asthmatic conditions thereto. In the past, methyl derivatives of arachidonic acid have been prepared. These derivatives relate to the inhibition of prostaglandin synthesis in order to treat disorders apparently arising therefrom.

In particular arachidonic acids methylated in the 2 or 3 position of the chain have been made by classical procedures wherein the intact arachidonic acid compound is methylated [Liang et al., Adv. Prost. Thrombox. Res. 6, 235 (1980)]. Also arachidonic acid analogs methylated in the 13 position have been disclosed by Yeh and Dawson, Tetrahedron Letters No. 49, pp. 4257–4260, (1977). This disclosure relates to compounds which have potential prostaglandin synthetase inhibitory activity.

SUMMARY OF THE INVENTION

In accordance with this invention, compounds are provided which inhibit the synthesis of SRS-A without inhibiting the synthesis of prostaglandins. The compounds of this invention are compounds of the formula

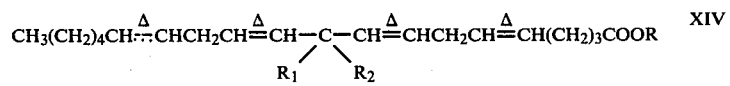

wherein Δ designates cis configuration across a double bond; the dotted line designates optionally a double bond or a hydrogenated bond; R represents hydrogen or lower alkyl; and $R_1$ and $R_2$ represent hydrogen or methyl with the proviso that where one of $R_1$ and $R_2$ is hydrogen the other is methyl; and pharamaceutically acceptable base addition salts thereof when R is hydrogen.

The compounds of formula XIV are prepared from novel intermediates of the formula

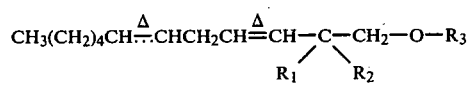

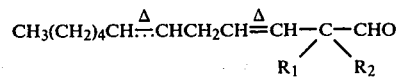

-continued $$R''(CH_2)_2CH\overset{\Delta}{=}CH(CH_2)_3CO_2R' \quad \text{XII}$$

wherein Δ, the dotted lines, $R_1$ and $R_2$ are as defined earlier; $R_3$ represents hydrogen or an ether protecting group; $R'$ represents lower alkyl and $R''$ represents a phosphonium salt whereby a compound of formula III is converted to a compound of formula V which is treated with a compound of formula XII to produce a compound of formula XIV.

The compounds of formulas III, V, XII and XIV are produced such that the stereo configuration about a carbon-carbon double bond is cis.

The compounds of formula XIV have been discovered to be potent inhibitors of SRS-A synthesis and, therefore, are useful as anti-allergic agents or anti-asthmatic agents; while compounds of formulas III, V and XII have been discovered to be useful in producing compounds of formula XIV. The compounds of formula XIV are specific inhibitors of SRS-A production, but such compounds do not significantly affect the biosynthesis of prostaglandins.

DETAILED DESCRIPTION OF INVENTION

The term "lower alkyl" comprehends both straight and branched chain saturated hydrocarbon groups having 1 to 7 carbon atoms, such as methyl, ethyl, propyl, isopropyl and the like.

The term "phosphonium salt" comprehends any phosphonium salt capable of forming a cis carbon-carbon double bond when such salt is condensed in a Wittig reaction with an aldehyde in the presence of a strong base. Among such phosphonium salts there are especially included the triaryl-phosphonium halides such as triphenyl or tritolylphosphonium halides. The triphenylphosphonium halide is preferred. Strong bases which may be employed in the Wittig reaction include such bases as lower alkyl-or aryllithium reagents, such as phenyllithium, methyllithium, n-butyllithium and the like, wherein n-butyllithium is preferred.

The term "halide" comprehends conventionally compounds containing a halogen which is inclusive of such atoms as bromine, chlorine, fluorine and iodine.

The term "ether protecting group" comprehends a hydrolyzable ether group removable by conventional hydrolysis or by acid catalyzed cleavage. Any conventional ether group that may be hydrolyzed by acid to yield a hydroxy group can be utilized as the ether protecting group. For example, ether protecting groups useful for the purpose of this invention include tetrahydropyranyl ethers, ethoxyethylethers, methoxy isopropyl ethers, and aryl or aryl lower alkyl ethers such as benzhydryl, trityl and the like.

Acid catalyzed cleavage of the ether protecting group may be carried out by conventional treatment with a strong organic or inorganic acid. Among the organic acids there are included lower alkanoic acids, i.e. acids having 2 to 7 carbon atoms, such as acetic acid, propionic acid and the like. Inorganic acids are preferred. Among the preferred inorganic acids are the mineral acids such as sulfuric acid, hydrochloric acid and the like. In carrying out this reaction, temperature and pressure are not critical, and this reaction may be carried out at room temperature and atmospheric pressure.

The term "cis" represented by $\Delta$ designates the fact that the two largest groups attached across a carbon-carbon double bond are on the same side of such double bond.

The compounds of formula XIV can be used in accordance with this invention in their salt form. Any conventional pharmaceutically acceptable base addition salts of the compounds of formula XIV may be utilized. Pharmaceutically acceptable base addition salts include any conventional non-toxic salt, such as the sodium salt, potassium salt, ammonium salt and the like, formed by neutralization of the acid form of compounds of formula XIV with an alkaline metal hydroxide or ammonium hydroxide.

The processes of the present invention relate to processes by which the cis configuration of the olefinic bonds in compounds of formula XIV are formed. These processes are summarized in the following reaction schemes I, II and III. For such reactions, temperature and pressure of the resulting reaction mixture are not critical, unless otherwise noted, and room temperature and atmospheric pressure are suitable for carrying out these reactions, as well as elevated or reduced temperatures and pressures. Where it is noted that a reaction is carried out under an inert atmosphere, any conventional inert gas can be utilized in a conventional manner to create the inert atmosphere. Generally such inert gases include, for example, argon, nitrogen or helium. A critical feature of each reaction is such that any resulting carbon-carbon double bond formed in a reaction product occurs in and is maintained in the cis configuration.

Reaction Scheme I

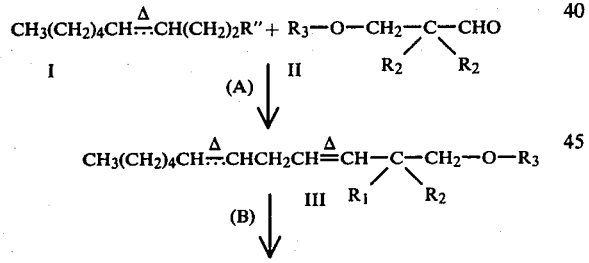

-continued
Reaction Scheme I

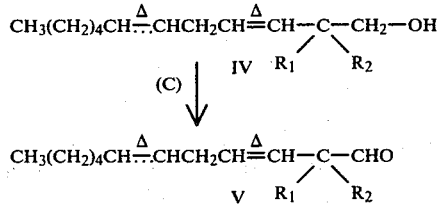

wherein $\Delta$, the dotted lines, $R_1$, $R_2$, $R''$ and $R_3$ are as defined earlier.

Reaction Scheme II

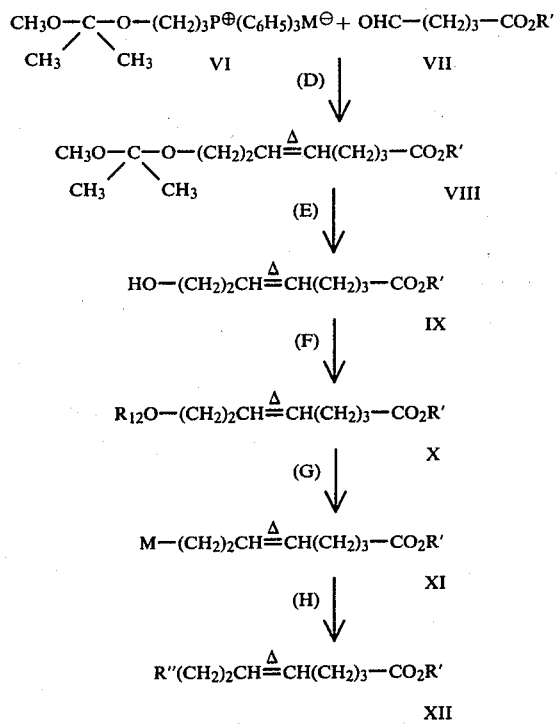

wherein $\Delta$, $R'$ and $R''$ are as defined earlier; $R_{12}$ represents lower alkyl or aryl sulfonyl; and M represents a halogen.

Reaction Scheme III

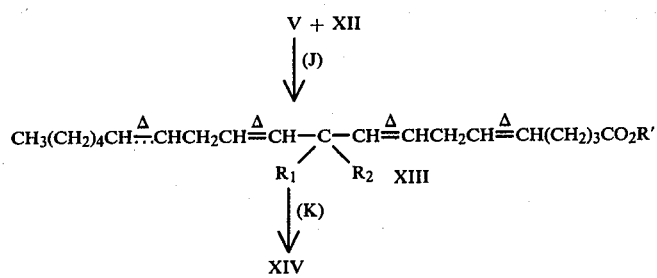

wherein $\Delta$, the dotted line, $R_1$, $R_2$ and $R'$ are as defined earlier.

Step A

In Step A of reaction Scheme I, the starting compounds are the compounds of formula I and II which are coupled via a Wittig reaction in a conventional manner to produce the compound of formula III. The weight ratio of compound of formula I to the compound of formula II is not critical but it is preferred that the compound of formula I be in stoichiometric excess to the compound of formula II. This reaction of step A is a condensation reaction between an aldehyde, e.g. a compound of formula II and a phosphonium halide salt, e.g. the compound of formula I in a cis-stereoselective Wittig reaction. This reaction is generally carried out using a deprotonating agent such as an alkyl or aryllithium base such as n-butyllithium in an ether solvent such as tetrahydrofuran and a co-solvent of tetrametyethylenediamine or hexamethylphosphorictriamide. Temperature and pressure for this reaction are not critical but it is preferred that the reaction be carried out between −30° C. and room temperature at atmospheric pressure.

It is an essential feature of this reaction step that the resulting carbon-carbon double bond formed in the reaction product, i.e., the compound of formula III, be in the cis configuration. Any of the conventional conditions used for producing such a cis configuration by a Wittig reaction can be used to carry out this step.

More particularly for example a compound of formula II such as the compound of formula

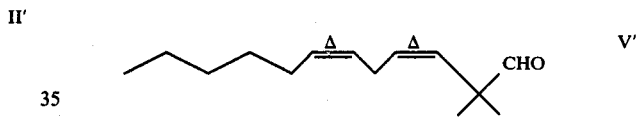

II' may be reacted via Wittig reaction with a compound of formula I such as the compound of formula

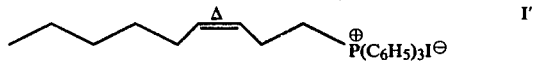

I' to produce a compound of formula III such as the compound of formula

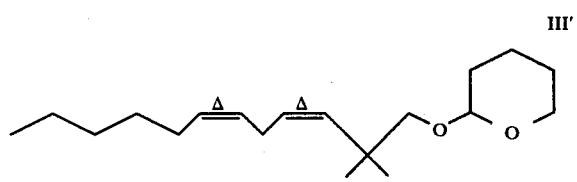

III' wherein Δ is as described earlier.

Step B

A compound of formula III is converted to a compound of formula IV in Step B of reaction Scheme I by hydrolysis of the ether bond formed by R₃ (an ether protecting group) to yield a hydroxy group in the compound of formula IV. This hydrolysis reaction may be carried out as described earlier utilizing conventional hydrolysis such as an acid catalyzed cleavage reaction of the ether protecting group.

More particularly for example a compound of formula III such as the compound of formula III' may be hydrolyed by an acid such as dilute hydrochloric acid to provide by the acid catalyzed cleavage the compound of formula

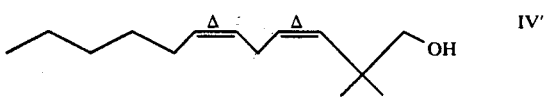

IV' wherein Δ is as described earlier.

Step C

The compound of formula IV is converted to the compound of formula V in Step C of reaction Scheme I by treating the compound of formula IV with an oxidizing agent. Any conventional oxidizing agent which may be utilized to convert a primary alcohol to an aldehyde can be used. Among the preferred oxidizing agents are included chromium trioxide dipyridine complex, pyridinium dichromate, and the like. Any of the conditions conventionally utilized with these oxidizing agents can be utilized in this conversion.

The compound of formula V resulting from the reaction of Step C of reaction Scheme I is employed in Step J of the reactions of reaction Scheme III.

More particularly for example a compound of formula IV such as the compound of formula IV' may be oxidized by treatment with a chromate oxidizing agent to provide the compound of formula

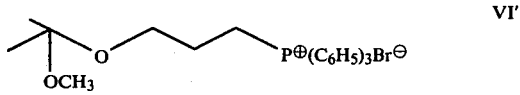

V'

Step D

In Step D of Reaction Scheme II, the starting compounds are the compounds of formula VI and VII which are coupled via a Wittig reaction in a conventional manner to produce the compound of formula VIII. The weight ratio of compound of formula VII to the compound of formula VI is not critical but it is preferred that the compound of formula VI be in stoichiometric excess to the compound of formula VII. This reaction of Step D is a condensation reaction between an aldehyde, e.g., a compound of formula VII and a phosphonium halide salt, e.g., the compound of formula VI in a cis-stereoselective Wittig reaction. This reaction is generally carried out as described earlier in Step A.

As in Step A, it is an essential feature of this reaction step that the resulting carbon-carbon double bond formed in the reaction product, i.e., the compound of formula VIII, be in the cis configuration.

More particularly for example a compound of formula VI such as the compound of formula

VI' may be reacted via Wittig reaction with a compound of formula VII such as a a compound of formula

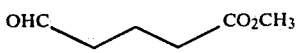

to produce a compound of formula VIII such as the compound of formula

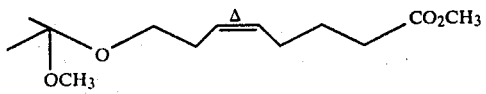

wherein Δ is as described earlier.

Step E

A compound of formula VIII is converted to a compound of formula IX in Step E of reaction Scheme II by hydrolysis of the ether bond in the compound of formula VIII to yield a hydroxy group in the compound of formula IX. This hydrolysis reaction may be carried out as described earlier utilizing conventional hydrolysis such as an acid catalyzed cleavage reaction of the ether protecting group.

More particularly for example a compound of formula VIII such as the compound of formula VIII' may be hydrolyzed by an acid such as dilute $H_2SO_4$ to provide by the acid catalyzed cleavage the compound of formula

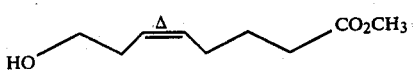

wherein Δ is as described earlier.

Step F

In Step F of reaction Scheme II, a compound of formula IX is activated by treating such compound in a conventional manner with a sulfonating agent to provide a compound of formula X. Any agent such as a lower alkyl or aryl sulfonyl halide which will react with the hydroxy group of the compound of formula IX to provide another group, i.e., an activated group for introducing a halide, may be used as the sulfonating agent. Among such agents are included for example such compounds as methanesulfonyl chloride, benzenesulfonyl chloride, p-toluenesulfonyl chloride (p-TsCl) and the like. Step F of reaction Scheme II may be by-passed to Step G wherein the compound of formula IX is halogenated conventionally by a halogenating agent to provide the compound of formula XI. For such a by-pass any of the conventional conditions for halogenating an alcohol via any conventional halogenating agent may be used to carry out a reaction of converting a compound of formula IX to a compound of formula XI. It is preferred, however, that Step F be performed in order to achieve a high yield in the halogenation process.

More particularly for example a compound of formula IX such as the compound of formula IX' may be reacted with a sulfonating agent such as p-toluenesulfonyl chloride to produce a compound of formula

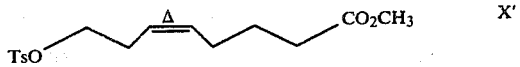

wherein Δ is as described earlier and Ts represents p-toluenesulfonyl.

Step G

A compound of formula X is halogenated in Step G to provide a compound of formula XI. The halogenation will replace the activated group of the compound of formula X with a halogen from a halogenating agent. The halogenating agent may be a halide salt such as for example an alkali metal halide such as NaI, LiI, KI, CsI and the like.

More particularly for example a compound of formula X such as the compound of formula X' may be reacted with a halogenating agent such as NaI conventionally to provide the compound of formula

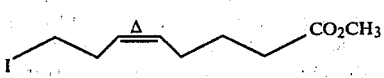

wherein Δ is as previously described.

Step H

A compound of formula XI is converted to the compound of formula XII in Step H by treating the compound of formula XI with a phosphine. Any phosphine which will react with a compound of formula XI to provide a phosphonium halide capable of condensation in a Wittig reaction with a compound of formula V to provide thereby the formation of a cis carbon-carbon double bond may be utilized as the phosphine. Among such phosphines are included for example the triarylphosphines such as triphenylphosphine and tritolyphosphine.

More particularly for example a compound of formula XI such as the compound of formula XI' may be treated with a phosphine agent such as triphenylphosphine to provide the compound of formula

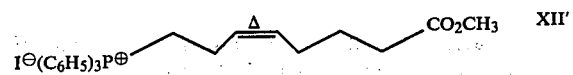

wherein Δ is as previously described.

Steps J and K

In Step J of reaction Scheme III, a compound of formula V is treated with a compound of formula XII in the presence of a strong base (such as the lower alkyl or aryllithium reagents previously referred to) to produce the compound of formula XIII utilizing a Wittig reaction. Any of the conditions conventional in condensing an aldehyde and a phosphonium salt, which permits formation of a cis carbon-carbon double bond, may be employed. Generally this reaction is initiated at low temperatures such as at a temperature of about −40° under an inert atmosphere at atmospheric pressure, and then brought to room temperature for conventional extraction of product after the reaction between the compound of formula V and formula XII has been completed.

The compound of formula XIII may be converted to the corresponding acid, a compound of formula XIV by any conventional saponification or hydrolysis or dealkylation reaction. For example saponification or hydrolysis may be effected by treating a compound of formula XIII with an alkali metal hydroxide such as NaOH, KOH, LiOH or the like at room temperature. While for example dealkylation may be effected by treating a compound of formula XIII with an alkali metal halide such as LiI, KI, CsI or the like in a pyridine solvent. Suitable pyridine solvents include pyridine and methylated pyridines such as collidine, lutidine and the like. It is preferred that dealkylation be carried out using lithium iodide in a pyridine solvent.

More particularly for example a compound of formula V such as the compound of formula V' may be condensed with a compound of formula XII such as the compound of formula XII' to provide the compound of formula

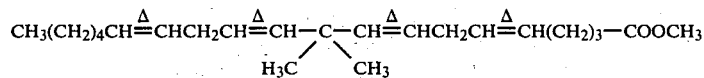
XIII' wherein Δ is as previously defined.

The compound of formula XIII' then can be converted by conventional hydrolysis to a compound of formula

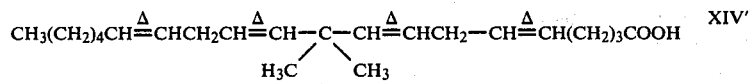
XIV' wherein Δ is as previously defined.

The novel compounds of formula XIV are potent inhibitors of SRS-A biosynthesis and therefore are useful as antiallergic agents or antiasthmatic agents; while compounds of formulae III, V and XII are useful as intermediates in producing compounds of formula XIV as by processes described above.

Prophylactically effective amounts of a compound of formula XIV, salts or esters thereof or pharmaceutical compositions containing prophylactically effective amounts of these compounds can be administered by methods well known in the art. Thus they can be administered, either singly or with other pharmaceutical agents, e.g., antagonists of mediators of anaphylaxis such as antihistamines, or antiasthmatic steroids such as prednisone and prednisolone, orally, parenterally or by inhalation, e.g., in the form of an aerosol, micropulverized powder or nebulized solution. For oral administration they can be administered in the form of pills, tablets, capsules, e.g., in admixture with talc, starch, milk sugar or other inert ingredients, i.e., pharmaceutically acceptable carriers, or in the form of aqueous solutions, suspensions, encapsulated suspensions, gels, elixirs or aqueous alcoholic solutions, e.g., in admixture with sugar or other sweetening agents, flavorings, colorants, thickeners and other conventional pharmaceutical excipients. For parenteral administration, they can be administered in solutions or suspensions, e.g., as an aqueous or peanut oil solution or suspension using excipients and carriers conventional for this mode of administration. For administration as aerosols, they can be dissolved in a suitable pharmaceutically acceptable solvent, e.g., ethyl alcohol or water or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, i.e., one which on activation releases a predetermined effective dose of the aerosol composition.

In practicing the method of the invention, the dose of compound of formula XIV or salts or esters thereof to be administered and the frequency of administration will be dependent on the potency and duration of activity of the particular compound to be administered and on the route of administration, as well as the severity of the condition, age of the mammal to be treated, etc. Doses of compound of formula XIV contemplated for use in practicing the method of the invention are about 0.01 to about 100 mg per kilogram of body weight per day, preferably about 0.1 to about 10 mg per kilogram of body weight per day, either as a single dose or in divided doses.

The following Examples are further illustrative of the invention but are not meant to restrict the invention in scope or spirit.

EXAMPLE 1

A 2.7 ml portion of n-butyllithium (1.6 M in hexane) was slowly added at −76° C., under argon to a solution of 2.7 g (5.24 mmoles) of (Z)-(3-nonenyl)-triphenylphosphonium iodide in a mixture of 7.5 ml of 2:1 tetrahydrofuran-hexamethylphosphorictriamide by syringe. The solution turned orange-red in color. Without delay, a solution of 0.700 g (3.76 mmoles) of 2,2-dimethyl-3-[(tetrahydro-2H-pyran-2-yl)oxy]-propanal in 1 ml of tetrahydrofuran was added dropwise to the solution. The resulting mixture was stirred at −78° C. for 30 minutes. The temperature was then allowed to rise to 0° C. After 1 hour, the reaction mixture was poured into brine, and the product extracted twice with 1:1 hexane-ether. The organic layer was dried using MgSO4, and the solvents evaporated in vacuo. Purification of the crude product by rapid chromatography on a silica-gel column gave 1.0 g (90.2%) of (Z,Z)-2-[(2,2-dimethyl-3,6-dodecadienyl)oxy]-tetrahydro-2H-pyran. This material was dissolved in 10 ml of methanol and treated with 0.1 ml of 2 N hydrochloric acid. After stirring for 2 hours at room temperature, the volume of methanol was reduced to about 3 ml by concentration under reduced pressure. The remaining solution was diluted with ether, and the ether solution washed with saturated sodium bicarbonate solution and brine and thereafter dried using MgSO4 and then concentrated under reduced pressure. The residue (0.780 g) was chromatographed on a silica gel column. Hexane-ether (4:1) eluted 0.690 g (79.1%) of pure (Z,Z)-2,2-dimethyl-3,6-dodecadien-1-ol. (98.6% pure by GC-analysis).

EXAMPLE 2

To a cooled solution of 2.25 g (27 mmoles) of pyridine in 30 ml of dichloromethane was added 1.38 g (13.8 mmoles) of chromium trioxide in portions. A solution of 0.345 g (1.65 mmoles) of (Z,Z)-2,2-dimethyl-3,6-dodecadien-1-ol in 5 ml of dichloromethane was slowly added to the stirred suspension at room temperature. After stirring at room temperature for 12 hours, the mixture was poured into 10% aqueous NaHCO3 solution and the product was extracted with ether. The ether extract was washed with brine, dried (MgSO4)

and concentrated in vacuo. The residue was chromatographed on silica gel. Elution with 9:1 hexane-ether afforded 0.195 g (57%) of (Z,Z)-2,2-dimethyl-3,6-dodecadienal.

EXAMPLE 3

To a suspension of 14.2 g (30 mmoles) of the 2-methoxy-2-propyl ether of (3-hydroxypropyl)triphenylphosphonium bromide in 150 ml of tetrahydrofuran and 30 ml of hexamethylphosphorictriamide was slowly added 19 ml of n-butyllithium (1.6 M in hexane), at −78° C., under argon. The solution quickly turned yellow in color. Without delay, 2.6 g (20 mmoles) of methyl 4-formylbutyrate in 30 ml of tetrahydrofuran was added, and the resulting mixture was stirred for 30 min. at −78° C., allowed to warm to room temperature, and then stirred for 1 hour at room temperature. To the reaction mixture was added 1 N $H_2SO_4$ solution (pH 1 to 2). After stirring for 1 hour at room temperature, the product was extracted with ether. The ether extracts were washed with brine, saturated aqueous $NaHCO_3$, and brine, then dried over $MgSO_4$ and concentrated under reduced pressure. The resultant oily material was chromatographed on silica gel to give 2.00 g (58.3%) of (Z)-8-hydroxy-5-octenoic acid methyl ester.

EXAMPLE 4

To a solution of 1.2 g (6.29 mmoles) of p-toluenesulfonylchloride in 4 ml of pyridine was slowly added 0.750 g (2.29 mmoles) of (Z)-8-hydroxy-5-octenoic and methyl ester in 1 ml of pyridine at room temperature. After stirring for 5 hours, the solution was poured into 2 N-sulfuric acid-ice, and the product was extracted with ether. The organic layer was washed with dilute sulfuric acid, saturated sodium bicarbonate and brine, then dried ($MgSO_4$), and the solvent was evaporated in vacuo. The residue was purified by rapid chromatography on a silica gel column to give 0.905 g (63.9%) of (Z)-8-[(4-methylphenyl)sulfonyl]oxy-5-octenoic acid methyl ester. This material was dissolved in 5 ml of acetone and slowly added to a solution of 1.81 g (12 mmoles) of sodium iodide in 10 ml acetone. The reaction mixture was stirred for 17 hrs. at room temperature and then diluted with water and extracted with hexane. The organic solution was washed with 10% sodium bisulfite and brine, then dried over $MgSO_4$, and the solvent removed in vacuo to give 0.775 g of crude product. Purification by rapid chromatography on a silica gel column followed by evaporative distillation afforded 0.500 g (63.7%) of (Z)-8-iodo-5-octenoic acid methyl ester (92.6% pure by GC analysis).

EXAMPLE 5

A 1.18 g (41.7 mmoles) sample of (Z)-8-iodo-5-octenoic acid methyl ester and 1.09 g (41.7 mmoles) sample of triphenylphosphine were heated, under argon, at 90° C. for 3 hours. This resulting solid, [(Z)-8-methoxy-8-oxo-3-octenyl]triphenylphosphonium iodide, was used in Example 6 without purification.

EXAMPLE 6

To a solution of 0.95 g (1.74 mmol) of [(Z)-8-methoxy-8-oxo-3-octenyl]triphenyl phosphonium iodide dissolved in 4.5 ml of a mixture of 2:1 tetrahydrofuran-hexamethylphosphorictriamide was added 0.85 ml of n-butyllithium (1.6 M in hexane) at −78° C., under argon. The solution quickly turned yellow-orange in color. A solution of 0.208 g (1.0 mmol) of (Z,Z)-2,2-dimethyl-3,6-dodecadienal in 0.2 ml of tetrahydrofuran was slowly added to the orange solution using a syringe. The reaction mixture was stirred for 30 min. at −78° C. and for an additional hour at 0° C., then treated with brine. The product was extracted with ether, and the ether extracts were washed with saturated ammonium chloride solution and brine. The organic phase was dried over $MgSO_4$, and the solvents evaporated at reduced pressure. The crude material was chromatographed on a silica gel column. Hexane-ether 9:1 eluted 0.288 g (83%) of (all Z)-10,10-dimethyleicosa-5,8,11,14-tetraenoic acid methyl ester which was dissolved in 4 ml of methanol and treated with 0.1 ml of an aqueous 5% potassium hydroxide solution. After 17 hrs. at room temperature, the reaction mixture was acidified with oxalic acid (pH ca. 1) and the product extracted with ether. The organic phase was washed with brine, dried over $MgSO_4$, and the solvent evaporated in vacuo. The crude product was purified by chromatography on silica gel to yield 0.104 g (38%) of (all Z)-10,10-dimethyleicosa-5,8,11,14-tetraenoic acid (>99% pure by GC analysis).

EXAMPLE 7

A mixture of 2.5 g (12 mmoles) of 1-bromononane and 3.16 g (12 mmoles) of triphenylphosphine was heated at 100° C. for 3 hrs. under argon. The resulting glassy (n-nonyl)triphenylphosphonium bromide (5.6 g) was used in Example 8 without purification.

EXAMPLE 8

A 5.6 g (11.9 mmoles) sample of (n-nonyl)triphenylphosphonium bromide was coupled with 1.86 g (10 mmoles) of the tetrahydropyranyl ether of hydroxypivaldehyde using the Wittig reaction conditions described in the previous examples (THF:HMPT, 2:1; 7 ml of 1.6 M n-butyllithium in hexane; −78° C.). The crude product (3.4 g) was chromatographed on silica gel. Hexane-ether (7:3) eluted 2.8 g (95%) of (Z)-2,2-dimethyl-3-dodecen-1-ol tetrahydropyranyl ether, which was dissolved in 28 ml of methanol and subsequently treated with 0.3 ml of 2 N HCl. After stirring for 3 hours at room temperature, most of the solvent (about 20 ml) was removed in vacuo, and the residue was extracted with ether. The ethereal solution was washed with brine, saturated $NaHCO_3$ solution, brine, dried over $MgSO_4$, and the solvent was evaporated under reduced pressure. The crude alcohol (2.2 g) was chromatographed on silica gel to afford 1.8 g (85%) of (Z)-2,2-dimethyl-3-dodecen-1-ol as an oil.

EXAMPLE 9

Using the procedure of Example 2, Z-2,2-dimethyl-3-dodecen-1-ol (0.9 g, 4.25 mmoles) was oxidized to (Z)-2,2-dimethyl-3-dodecenal (0.612 g, 68.5% after chromatographic purification) by Collins reagent (3.55 g of $CrO_3$, 5.85 ml of pyridine in 80 ml of methylene chloride).

EXAMPLE 10

A 1.34 g (2.46 mmoles) sample of [(Z)-8-methoxy-8-oxo-3-octenyl]triphenylphosphonium iodide was condensed with 0.400 g (1.9 mmoles) of (Z)-2,2-dimethyl-3-dodecenal using the Wittig reaction conditions described in previous examples (THF-HMPT, 2.5:1; 1.2 ml of 1.6 M n-butyllithium in hexane; −78° C.). The resultant oily (all Z)-10,10-dimethyl-5,8,11-eicosatrienoic acid methyl ester (0.323 g, 49%) was saponified with KOH in methanol (6 drops of 5% aqueous KOH in 6 ml of methanol) to yield 0.214 g (69%) of (all Z)-10,10-dimethyl-5,8,11-eicosatrienoic acid as an oil after chromatographic purification.

EXAMPLE 11

Inhibition of the In Vitro Synthesis of SRS-A in Rat Peritoneal Cells

To study the effect of drugs on SRS-A synthesis in rat peritoneal cells, these cells (including mast cells, monocytes, eosinophils and neutrophils) were isolated from male Sprague-Dawley rats (Charles River Laboratories) weighing 180–220 g by the lavage procedure described by Herzig, D. G. and Dusner, E. J. Journal of Pharmacology and Experimental Therapeutics, 194, 457–460 (1975) with the exception that Hanks balanced salt solution used in these experiments was adjusted to pH 6.9 with 5% (V/V) of 0.1 M aqueous phosphate buffer and contained 50 mg/ml sodium heparin. After removal from the peritoneal cavity of rats, the cells were subsequently isolated by centrifugation at 400×gravity for 10 minutes at 4° C. and resuspended to a concentration of about 2,000,000 cells per ml in Hanks buffer.

Samples for evaluation were prepared by adding various concentrations of test drugs to 2 ml aliquots of resuspended cells in Hanks buffer. The 2 ml samples used for control contained 2 ml aliquots of resuspended cells in Hanks buffer without drugs. All of the above samples (2 ml final volume) were preincubated at 37° C. for 10 minutes in the presence of varying concentrations of test drug prior to challenge with $5 \times 10^{-7}$ M ionophore A23187. This ionophore is disclosed in Burka and Flower, Br. J. Pharmacology 65: 35-41 (1979). Antibiotic A 23187 was used as a probe for the study of calcium and function in biological systems. After ionophore challenge, SRS-A was synthesized in the samples by the cells for 10 minutes (at 37° C.) after which this synthesis was terminated by placing the samples in a boiling water bath for 10 minutes followed by centrifugation at $2,000 \times g$ (10 minutes) at 4° C. to remove coagulated protein and cellular debris. The SRS-A present in the resulting supernatants was quantitated by a bioassay using a guinea pig ileum as described in Orange, and Austen, Adv. Immunol, 10:105-144 (1969). For this bioassay, a 1.5 cm segment of ileum was removed from animals weighing 300 to 400 g and resuspended in an organ bath containing 10 ml of Tyrodes solution with $10^{-6}$ M atropine sulfate and $10^{-6}$ M pyrilamine maleate. The bath was maintained at 37° C. and aerated with a mixture of 95% $O_2$ and 5% $CO_2$. The concentration of SRS-A in the experimental samples was determined by a comparison of isotonic contraction responses elicited by the samples with those obtained with varying amounts of an SRS-A standard procedures of Orange, R. R. and Austen, K. F. Adv. Immunol. 10:105-144 (1969) against histamine (1 unit of SRS-A being that amount which gives a contractile response similar to that of 5 mg of histamine). In the absence of drug, the ionophore A23187-induced SRS-A synthesis varied between 40 to 50 units of SRS-A per $10^6$ cells. In the presence of increasing concentrations of test drug, there was a concentration-related decrease in SRS-A synthesis.

The mean percent inhibition $$\frac{\text{difference of units of SRS-A in test sample}}{\text{units of SRS-A in control sample}} \times 100$$

at each concentration of the various test drugs was calculated. The concentration of test drug which inhibits the synthesis of SRS-A by 50% ($IC_{50}$) was determined for each test drug from a plot of the mean percent inhibition versus drug concentration. Both the % inhibition at 10 $\mu$M and the $IC_{50}$ are given in following Table I. The difference of units of SRS-A in the test sample used in the fraction given above was obtained by subtracting the units of SRS-A in the control from the actual measurement of the units of SRS-A in the sample.

TABLE I

| Test drug | % Inhibition at 10 $\mu$M | $IC_{50}$ ($\mu$M) |
|---|---|---|
| (All Z)-10,10-Dimethyl-5,8,11,14-eicosatetra-enoic Acid | 99 ± 1 (p < 0.001) | 1–3 |
| (All Z)-10,10-Dimethyl-5,8,11-eicosatrienoic Acid | 100 ± 0 (p < 0.001) | <10 |

EXAMPLE 12

| Capsule Formulation of (All Z)-10,10-Dimethyl-5,8,11,14-eicostetraenoic acid | | | | | |
|---|---|---|---|---|---|
| Item | Ingredients | | mg/capsule | | |
| 1. | (All Z)-10,10-Dimethyl 5,8,11,14-eicostetraenoic acid | 0.1 | 0.5 | 5.0 | 10.0 | 25.0 |
| 2. | Lactose | 183.9 | 183.5 | 179.0 | 218.0 | 257.0 |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium Stearate | 1.0 | 1.0 | 1.0 | 2.0 | 3.0 |
| | Total | 220 mg | 220 mg | 220 mg | 290 mg | 370 mg |

Procedures:
1. Mix Items 1–3 in a suitable mixer. Mill through a suitable mill.
2. Mix with Items 4 and 5 and fill on capsule machine.

EXAMPLE 13

| Tablet Formulation (Wet Granulation) of (all Z)-10,10-Dimethyl-5,8,11,14-eicosatetraenoic acid | | | | | |
|---|---|---|---|---|---|
| Item | Ingredients | | mg/capsule | | |
| 1. | (All Z)-10,10-Dimethyl-5,8,11,14-eicosatetraenoic acid | 0.1 | 0.5 | 5.0 | 10.0 | 25.0 |

-continued
Tablet Formulation (Wet Granulation) of (all Z)-10,10-Dimethyl-5,8,11,14-eicosatetraenoic acid

| Item | Ingredients | mg/capsule | | | | |
|---|---|---|---|---|---|---|
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregelatinized Starch | 10.0 | 10.0 | 10.0 | 20.0 | 30.0 |
| 5. | Magnesium Stearate | 1.0 | 1.0 | 1.0 | 2.0 | 3.0 |
| | Total | 125 mg | 125 mg | 125 mg | 200 mg | 285 mg |

Procedure:
1. Mix Items 1-5 in a suitable mixer, granulate with water. Dry, mill.
2. Mix with Item 5 and compress on a suitable press.

EXAMPLE 14

Tablet Formulation (Direct Compression) of (All Z)-10,10-Dimethyl-5,8,11,14-eicosatetraenoic acid

| Item | Ingredients | mg/capsule | | | | |
|---|---|---|---|---|---|---|
| 1. | (All Z)-10,10-Dimethyl-5,8,11,14-eicosatetraenoic acid | 0.1 | 0.5 | 5.0 | 10.0 | 25.0 |
| 2. | Lactose | 85.4 | 85.5 | 81.0 | 103.0 | 112.5 |
| 3. | Avicel | 30.0 | 30.0 | 30.0 | 45.0 | 60.0 |
| 4. | Modified Starch | 8.0 | 7.5 | 7.5 | 10.0 | 15.0 |
| 5. | Magnesium Stearate | 1.5 | 1.5 | 1.5 | 2.0 | 2.5 |
| | Total | 125 mg | 125 mg | 125 mg | 170 mg | 215 mg |

Procedure:
1. Mix Items 1-5 in a suitable mixer for 10-15 minutes.
2. Add magnesium stearate (Item 5) as a premix and mix for 4 minutes.
3. Compress on a suitable press.

EXAMPLE 15

Capsule Formulations of (All Z)-10,10-Dimethyl-5,8,11-eicosatrienoic acid

| Item | Ingredients | mg/capsule | | | | |
|---|---|---|---|---|---|---|
| 1. | (All Z)-10,10-Dimethyl-5,8,11-eicosatrienoic acid | 0.1 | 0.5 | 5.0 | 10.0 | 25.0 |
| 2. | Lactose | 183.9 | 183.5 | 179.0 | 218.0 | 257.0 |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium Stearate | 1.0 | 1.0 | 1.0 | 2.0 | 3.0 |
| | Total | 220 mg | 220 mg | 220 mg | 290 mg | 370 mg |

Procedures:
1. Mix Items 1-3 in a suitable mixer. Mill through a suitable mill.
2. Mix with Items 4 and 5 and fill on capsule machine.

EXAMPLE 16

Tablet Formulation (Direct Compression) of (All Z)-10,10-Dimethyl-5,8,11-eicosatrienoic acid

| Item | Ingredients | mg/tablet | | | | |
|---|---|---|---|---|---|---|
| 1. | (All Z)-10,10-Dimethyl-5,8,11-eicosatrienoic acid | 0.1 | 0.5 | 5.0 | 10.0 | 25.0 |
| 2. | Lactose | 85.4 | 85.5 | 81.0 | 103.0 | 112.5 |
| 3. | Avicel | 30.0 | 30.0 | 30.0 | 45.0 | 60.0 |
| 4. | Modified Starch | 8.0 | 7.5 | 7.5 | 10.0 | 15.0 |
| 5. | Magnesium Stearate | 1.5 | 1.5 | 1.5 | 2.0 | 2.5 |
| | Total | 125 mg | 125 mg | 125 mg | 170 mg | 215 mg |

Procedures:
1. Mix Items 1-5 in a suitable mixer for 10-15 minutes.
2. Add magnesium stearate (Item 5) as a premix and mix for 4 minutes.
3. Compress on a suitable press.

EXAMPLE 17

Tablet Formulation (Wet Granulation) of (All Z)-10,10-Dimethyl-5,8,11-eicosatrienoic acid methyl ester

| Item | Ingredients | mg/tablet | | | | |
|---|---|---|---|---|---|---|
| 1. | (All Z)-10,10-Dimethyl-5,8,11-eicosatrienoic | 0.1 | 0.5 | 5.0 | 10.0 | 25.0 |

-continued

Tablet Formulation (Wet Granulation) of
(All Z)-10,10-Dimethyl-5,8,11-eicosatrienoic acid methyl ester

| Item | Ingredients | mg/tablet | | | | |
|---|---|---|---|---|---|---|
| | acid | | | | | |
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregelatinized Starch | 10.0 | 10.0 | 10.0 | 20.0 | 30.0 |
| 5. | Magnesium Stearate | 1.0 | 1.0 | 1.0 | 2.0 | 3.0 |
| | Total | 125 mg | 125 mg | 125 mg | 200 mg | 285 mg |

Procedure:
1. Mix Items 1-5 in a suitable mixer, granulate with water. Dry, mill.
2. Mix with Item 5 and compress on a suitable press.

EXAMPLE 18

Capsule Formulation (All Z)-10-methyleicosa-5,8,11,14-tetraenoic acid

| Item | Ingredients | mg/capsule | | | | |
|---|---|---|---|---|---|---|
| 1. | (All Z)-10-methyleicosa-5,8,11,14-tetraenoic acid | 0.1 | 0.5 | 5.0 | 10.0 | 25.0 |
| 2. | Lactose | 183.9 | 183.5 | 179.0 | 218.0 | 257.0 |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium Stearate | 1.0 | 1.0 | 1.0 | 2.0 | 3.0 |
| | Total | 220 mg | 220 mg | 220 mg | 290 mg | 370 mg |

Procedures:
1. Mix Items 1-3 in a suitable mixer. Mill through a suitable mill.
2. Mix with Items 4 and 5 and fill on capsule machine.

EXAMPLE 19

Tablet Formulation (Wet Granulation) of
(All Z)-10-methyleicosa-5,8,11,14-tetraenoic acid

| Item | Ingredients | mg/capsule | | | | |
|---|---|---|---|---|---|---|
| 1. | (All Z)-10-methyleicosa-5,8,11,14-tetraenoic acid | 0.1 | 0.5 | 5.0 | 10.0 | 25.0 |
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregelatinized Starch | 10.0 | 10.0 | 10.0 | 20.0 | 30.0 |
| 5. | Magnesium Stearate | 1.0 | 1.0 | 1.0 | 2.0 | 3.0 |
| | Total | 125 mg | 125 mg | 125 mg | 200 mg | 285 mg |

Procedure:
1. Mix Items 1-5 in a suitable mixer, granulate with water. Dry, mill.
2. Mix with Item 5 and compress on a suitable press.

EXAMPLE 20

Tablet Formulation (Direct Compression) of
(All Z)-10-methyleicosa-5,8,11,14 tetraenoic acid

| Item | Ingredients | mg/capsule | | | | |
|---|---|---|---|---|---|---|
| 1. | (All Z)-10-methyleicosa-5,8,11,14 tetraenoic acid | 0.1 | 0.5 | 5.0 | 10.0 | 25.0 |
| 2. | Lactose | 85.4 | 85.5 | 81.0 | 103.0 | 112.5 |
| 3. | Avicel | 30.0 | 30.0 | 30.0 | 45.0 | 60.0 |
| 4. | Modified Starch | 8.0 | 7.5 | 7.5 | 10.0 | 15.0 |
| 5. | Magnesium Stearate | 1.5 | 1.5 | 1.5 | 2.0 | 2.5 |
| | Total | 125 mg | 125 mg | 125 mg | 170 mg | 215 mg |

Procedure:
1. Mix Items 1-5 in a suitable mixer for 10-15 minutes.
2. Add magnesium stearate (Item 5) as a premix and mix for 4 minutes.
3. Compress on a suitable press.

EXAMPLE 21

Capsule Formulations of (All Z)-10-methyleicosa-5,8,11-trienoic acid

| Item | Ingredients | mg/tablet | | | | |
|---|---|---|---|---|---|---|
| 1. | (All Z)-10-methyleicosa-5,8,11-trienoic acid | 0.1 | 0.5 | 5.0 | 10.0 | 25.0 |
| 2. | Lactose | 183.9 | 183.5 | 179.0 | 218.0 | 257.0 |

-continued

| Capsule Formulations of (All Z)-10-methyleicosa-5,8,11-trienoic acid | | | | | |
|---|---|---|---|---|---|
| Item | Ingredients | | mg/tablet | | |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium Stearate | 1.0 | 1.0 | 1.0 | 2.0 | 3.0 |
| | Total | 220 mg | 220 mg | 220 mg | 290 mg | 370 mg |

Procedures:
1. Mix Items 1-3 in a suitable mixer. Mill through a suitable mill.
2. Mix with items 4 and 5 and fill on capsule machine.

EXAMPLE 22

| Tablet Formulation (Direct Compression) of (All Z)-10-methyleicosa-5,8,11-trienoic acid | | | | | |
|---|---|---|---|---|---|
| Item | Ingredients | | mg/tablet | | |
| 1. | (All Z)-10-methyleicosa-5,8,11-trienoic acid | 0.1 | 0.5 | 5.0 | 10.0 | 25.0 |
| 2. | Lactose | 85.4 | 85.5 | 81.0 | 103.0 | 112.5 |
| 3. | Avicel | 30.0 | 30.0 | 30.0 | 45.0 | 60.0 |
| 4. | Modified Starch | 8.0 | 7.5 | 7.5 | 10.0 | 15.0 |
| 5. | Magnesium Stearate | 1.5 | 1.5 | 1.5 | 2.0 | 2.5 |
| | Total | 125 mg | 125 mg | 125 mg | 170 mg | 215 mg |

Procedure:
1. Mix Items 1-5 in a suitable mixer for 10-15 minutes.
2. Add magnesium stearate (Item 5) as a premix and mix for 4 minutes.
3. Compress on a suitable press.

EXAMPLE 23

| Tablet Formulation (Wet Granulation) of (All Z)-10-methyleicosa-5,8,11-trienoic acid | | | | | |
|---|---|---|---|---|---|
| Item | Ingredients | | mg/tablet | | |
| 1. | (All Z)-10-methyleicosa-5,8,11-trienoic acid | 0.1 | 0.5 | 5.0 | 10.0 | 25.0 |
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregelatinized Starch | 10.0 | 10.0 | 10.0 | 20.0 | 30.0 |
| 5. | Magnesium Stearate | 1.0 | 1.0 | 1.0 | 2.0 | 3.0 |
| | Total | 125 mg | 125 mg | 125 mg | 200 mg | 285 mg |

Procedure:
1. Mix Items 1-5 in a suitable mixer, granulate with water. Dry, mill.
2. Mix with Item 5 and compress on a suitable press.

What is claimed is:

1. A compound of the formula:

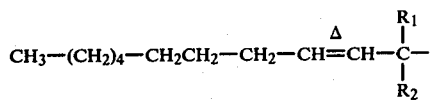

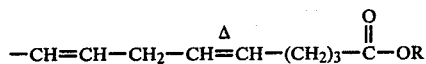

wherein $\Delta$ designates a cis configuration, R is hydrogen or lower alkyl; and $R_1$ and $R_2$ are hydrogen or methyl with the proviso that where one of $R_1$ and $R_2$ is hydrogen the other is methyl, and pharmaceutically acceptable salts thereof where R is hydrogen.

2. A compound according to claim 1 which is (all Z)-10,10-dimethyleicosa-5,8,11-trienoic acid.

3. A compound according to claim 1 which is (all Z)-10-methyleicosa-5,8,11-trienoic acid.

* * * * *